United States Patent [19]

Hudson et al.

[11] Patent Number: 4,485,116

[45] Date of Patent: Nov. 27, 1984

[54] ANTIPROTOZOAL COMPOUNDS

[76] Inventors: Alan T. Hudson, Lustleigh, Stonehouse La., Halstead, Sevenoaks, Kent; Anthony W. Randall, 27 Hayes Garden, Hayes, Kent, both of England

[21] Appl. No.: 433,866

[22] Filed: Oct. 13, 1982

[30] Foreign Application Priority Data

Oct. 16, 1981 [GB] United Kingdom ............... 8131206
Jul. 16, 1982 [GB] United Kingdom ............... 8220680

[51] Int. Cl.³ ..................... A01N 9/24; C07C 50/12
[52] U.S. Cl. ................................. 424/331; 260/396 R
[58] Field of Search .................. 260/396 R; 424/331, 424/251, 253, 258

[56] References Cited

U.S. PATENT DOCUMENTS

| | | | |
|---|---|---|---|
| 2,553,647 | 5/1951 | Fieser ................................. | 266/396 |
| 3,347,742 | 10/1967 | Rogers ................................ | 424/331 |
| 3,393,211 | 7/1968 | Fisher et al. ....................... | 260/396 |
| 3,578,686 | 5/1971 | Tullar et al. ....................... | 424/331 |
| 3,682,991 | 8/1972 | Tullar et al. ....................... | 424/331 |
| 4,110,473 | 8/1978 | Fugitt et al. ....................... | 424/331 |

FOREIGN PATENT DOCUMENTS 2228 6/1979 European Pat. Off. ............ 424/331

Primary Examiner—Glennon H. Hollrah
Assistant Examiner—Raymond Covington
Attorney, Agent, or Firm—Donald Brown

[57] ABSTRACT

1,4-Naphthoquinones of formula (I), methods for their preparation, veterinary formulations thereof, and the use thereof in animal therapy are disclosed.

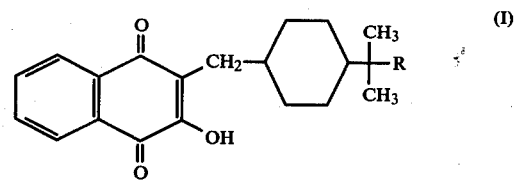

Particularly preferred compounds of formula (I) are, 2-[trans-(4-t-butylcyclohexyl)methyl]-3-hydroxy-1,4-naphthoquinone, and 2-[trans-(4-t-pentyl cyclohexyl)-methyl]3-hydroxy-1,4-naphthoquinone. The compounds are of value as anti-protozoal agents, in particular as anti-theilerial agents.

16 Claims, No Drawings

ANTIPROTOZOAL COMPOUNDS

The present invention relates to compounds and preparations for treating and preventing theileriosis in cattle and sheep, and to processes for the synthesis of such compounds.

Theileriosis is a disease caused by protozoa of the genus Theileria. In cattle, *T.Parva*(parva), *T.Parva*(lawrencei), *T.Parva*(Bovis), *T.Sergenti, T.annulata* and *T.mutans* are responsible for substantial losses, mainly in Central and East Africa, and the Middle East. In sheep, *T.hirci* and *T.ovis* are the causative agents and the disease is prevalent in the Middle East. Infected ticks transmit these protozoa to the mammalian host. The lymphocyte cells are infected which then proceed to divide rapidly contrary to their normal function. Death is caused by the release of toxic products from rupturing lymphocytes in addition to other harmful effects attributed to the parasites themselves. After release from the lymphocytes, the Theileria parasite infects the erythrocytes and then the ticks, which feed on the infected animals.

In the field there is no known effective treatment of theileriosis. Compounds having anti-theilerial activity are known but are toxic to the host, and their use is precluded for the treatment of theilerial infections. The only drug that has hitherto been used for the treatment of cattle and sheep is oxytetracycline (Terramycin), the usual use of which is against anaplasmosis and bacterial infections. According to S. F. Barnett in Infectious Blood Diseases of Man and Animals, Vol. III, Eds. Weinman D. & Ristic M., Academic Press 1968, this compound has had only very limited success when given before an infection is established, but no effect once the infection is actually established. Frequently, the symptoms of anaplasmosis are misinterpreted and theileriosis is diagnosed, and as a result oxytetracycline is administered, often in massive doses up to nearly the toxic level. Apparent recovery from theileriosis is in actual fact real recovery from anaplasmosis, and bacterial infections.

British Pat. No. 1,553,424 describes 2-hydroxy-3-cyclohexylalkyl and 2-hydroxy-3-cyclohexyl-1,4-naphthoquinone derivatives as effective for the prevention and treatment of theileriosis. Subsequently, it has been found that the latter compound, 2-hydroxy-3-cyclohexyl-1,4-naphthoquinone is therapeutically the most effective compound, and in particular is most effective against infections with *T.parva*.

European Patent Application No. 78,101,426 refers, inter alia, to 3-hydroxy-1,4-naphthoquinones in which the substituent in the 2-position is a $C_{3-12}$cycloalkyl ring optionally bearing as a substituent a $C_{1-4}$alkyl group, in particular a methyl group. However no specific compounds bearing a substituent are disclosed, nor is there any indication of which positions of the cycloalkyl ring are to be substituted.

Compounds of formula (I) below have been disclosed in our co-pending UK application No. 8131206, as intermediates in the preparation of certain 2-substituted-3-hydroxy-1,4-naphthoquinones. It has now been found that the compounds of formula (I) below show high and advantageous activity against various *Theileria species* in tests under in vivo and in vitro conditions and in contrast to the compounds of British Pat. No. 1,553,424, are notably effective against infections with *T.annulata*. This enables the preparation of novel therapeutic compositions and the treatment of animals against the diseases caused by these organisms.

According to one aspect of the invention there is provided a compound of formula (I), a tautomer, or a pharmaceutically acceptable salt thereof,

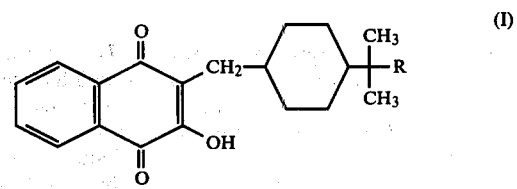

wherein R is an alkyl group of from 1 to 10 carbon atoms.

Tautomerism may cause the 3-hydroxy group to donate its acidic hydrogen to the adjacent oxo group, but it is believed that formula (I) represents the more stable state. Since the hydroxy group in the formula may form salts with appropriate bases, the pharmaceutically acceptable salts of the compounds include those with an alkali metal cation, such as sodium or potassium, and those with organic bases such as ethanolamine, diethanolamine and N-methyl glucamine.

It will be appreciated that the compounds of formula (I) may exist as cis or trans isomers, that is to say that the cyclohexyl ring may be cis or trans substituted by the naphthoquinone-methylene residue and the 4-t-alkyl group. The invention includes both cis and trans isomers and mixtures thereof in any ratio.

It should be noted that in the unsubstituted 1,4-naphthoquinone ring the 2 and 3 positions are identical and thus, in the naming of the compounds, convention will dictate whether the cyclohexyl substituent or the hydroxyl group is in the 2 position. For convenience throughout this specification when the compounds are referred to non-specifically the substituent is defined as in the 2 position.

In the compounds of formula (I), R is suitably a straight chain $C_{1-4}$ alkyl group. The preferred group is methyl or ethyl.

The compounds of formula (I) may be prepared by any method known in the art for the preparation of compounds of analagous structure.

For example, the compounds of formula (I) may be prepared from compounds of formula (II), wherein R, is as herein defined, by standard literature methods for converting such compounds to 3-hydroxy-1,4-naphthoquinones. Compounds of formula (II) may be prepared from compounds of formula (IIA) by Fries rearrangement.

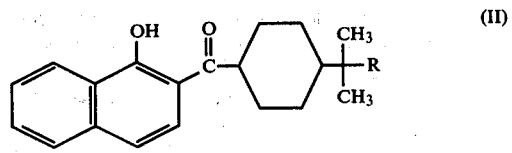

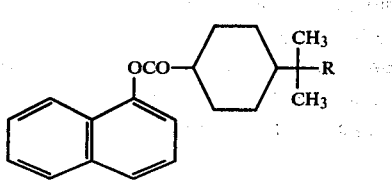

(IIA)

Alternatively, compounds of formula (I) may be prepared by conversion of the corresponding 3-halogeno-, e.g. 3-chloro- or 3-bromo, analogues of formula (III) in which X is halogen and R is as defined above into the 3-hydroxy-substituted compounds by alkaline hydrolysis, for example with an alkali metal hydroxide in a suitable medium. For instance potassium hydroxide in aqueous methanolic medium has been found convenient. The starting 3-halogeno derivative may be obtained by oxidation and subsequent halogenation from the corresponding substituted 4a, 5, 7, 7a-tetrahydro-2-cyclohexylmethyl-1,4-naphthoquinone according to the method suggested by Fieser, L., (J. Am. Chem. Soc., 1948,3165) originally starting from a substituted or unsubstituted 2-cyclohexylmethylphenol.

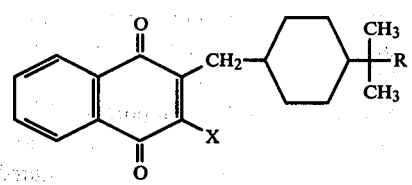

(III)

In a further alternative method compounds of formula (I) may be prepared by introduction of a hydroxy group into the 3 position of compounds of formula (IV):

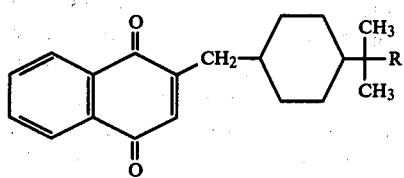

(IV)

wherein R is as defined herein.

Thus for example, the compounds of formula (I) may be halogenated (eg chlorinated or brominated) to provide compounds of formula (III) above which may then be converted to compounds of formula (I) as described above.

Compounds of formula (IV) may also be epoxidised to provide a compound of formula (V)

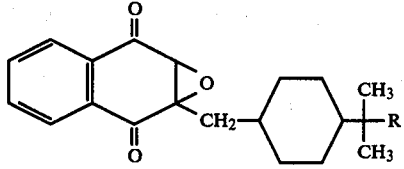

(V)

which may then be hydrolysed to a compound of formula (I) for example with dilute aqueous base or dilute aqueous acid.

The compound of formula (IV) may also be subjected to a Thiele acetylation by reaction with an appropriate acetylating agent (eg acetic anhydride) in the presence of an oxidising agent (eg perchloric acid) to provide compounds of formula (VIa). Compounds of formula (VIa) may be converted to compounds of formula (VIb) by hydrolysis which compounds may be converted to compounds of formula (I) by oxidation eg. by a method analogous to that described in Organic Reactions, vol 19 p222. Suitable oxidising agents include, for example, ferric chloride and mineral acid or chromic acid.

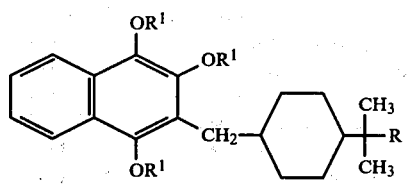

(VI)

(a) $R^1 = COCH_3$
(b) $R^1 = H$

In the above processes the stereochemistry of the final product will reflect that of the starting materials. Thus if stereochemically pure compounds are used as reactants the pure cis or pure trans isomer will result.

In a further preferred alternative, compounds of formula (I) may be prepared by reacting a compound of formula (VII)

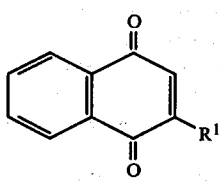

(VII)

wherein $R^1$ is halogeno e.g. chloro or bromo atoms, or a hydroxy, acetoxy or alkoxy group with a cyclohexylmethyl donor compound containing the R moiety as hereinbefore defined in a form capable of providing the substituted cyclohexylmethyl group as a free radical and, if desired, hydrolysing the $R^1$ group other than hydroxy into a 3-hydroxy group in the resulting 2-cyclohexylmethyl substituted condensate.

A preferred donor is the corresponding substituted cyclohexyl acetic acid which may undergo oxidative decarboxylation. For instance persulphate with a catalyst, such as silver ions, is convenient for the purpose, (c.f.Jacobson N. et al., Annalen, 1972, 763, 135 and Acta Chem. Scand, 1973,27, 3211). Preferably, when persulphate is used under those conditions, the reaction is carried out with a 1,4-naphthoquinone substituted for $R^1$ with a group other than hydroxy. Conveniently ammonium persulphate can be used as the oxidising agent, and the catalyst is silver nitrate. Hydrolysis subsequent to the main coupling reaction, may if required, provide the hydroxy group. Alkaline conditions are usually preferred for the hydrolysis.

An example for the donor carrying itself a peroxide grouping is the method employing an appropriately substituted cyclohexylmethylalkanoyl peroxide as suggested by U.S. Pat. No. 2,553,647.

The provision of the cycloalkyl free radical by a spontaneous release from the donor can for instance be achieved by the use of a tricyclohexylmethyl-borane. Such reagent can be prepared by reacting the cycloalkene with borane dimethylsulphide. Conveniently the reaction is carried out in a solvent such as tetrahydrofuran. The 2-substituted-1,4-naphthoquinones required for some of the above reaction schemes, are available by synthetic processes known in themselves from the literature, e.g. Fieser, L., J. Am. Chem. Soc., 1948, 3165, or prepared accordingly by analogous techniques.

Also of use as a cyclohexyl donor is the corresponding substituted cyclohexyl carboxylic acid; if used it will be clear to those skilled in the art that an addition step of reduction of the alkene will be required following condensation to provide compound of formula (I).

It will be appreciated by those skilled in the art that the above process will lead to a mixture of cis and trans isomers.

Where a single isomer, cis or trans, of a compound of formula (I) is desired this may be obtained by means of isomerically pure starting materials in those reactions above in which isomerisation does not occur. In particular, use of stereo specifically pure carboxylic acid in the final process described above. If a mixture of isomers is obtained the mixture may be separated by physical means. Such methods are well known in the art, and include for example fractional crystallisation or chromatographic separation.

A further aspect of the present invention provides compounds of formula (VIII)

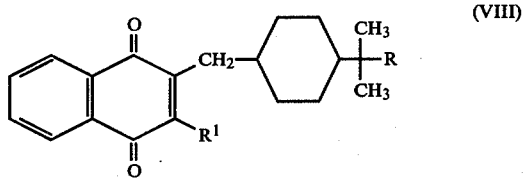

wherein R is as defined herein above, and $R^1$ is as herein defined above or a benzyloxy group. These compounds are useful as intermediates in the above syntheses. Those which carry a group for $R^1$ which is easily hydrolysed in vivo into the hydroxy group, may be used as pro-drugs in formulations or for treatment to provide the hydrolysed end-product in situ. The acetyl or benzoyl group may undergo such hydrolysis and could therefore be used as long acting precursors of active compounds.

The compounds of formula (I) have been found to be extremely active against protozoa of the genus Theileria, and are thus of use in the treatment and/or prophylaxis of theileriosis in cattle and sheep. In particular the compounds have been found to be active against infection with T.annulata.

It will be appreciated that the amount of compound of formula (I) required for use in the treatment or prophylaxis of theilerial infections will vary not only with the active compound, but also with the route of administration and nature of the infection.

The "effective amount, dosage or unit-dosage" as used herein is denoted to mean a predetermined amount of the compound which is sufficiently effective against Theileria organisms, for instance in cattle or sheep when administered in vivo. To contribute to or achieve prophylaxis or cure, some preparations may contain multiples of the dosage required by a single animal.

A typical initial dose for cattle weighing 400 kg may be 0.2 to 10 g. conveniently 0.5 to 2.5 g., and for calves or sheep 50 mg to 1.0 g., or preferably about 0.1 to 0.5 gramme of the active compound, but further dosages may be given.

While it is possible that, for use as anti-theilerial agents, the compounds of formula (I) may be administered as the raw chemical, it is preferable to present the active ingredient as a therapeutic preparation.

The therapeutic preparations comprising compound of formula (I), may take the form of shaped tablets or a composition with pharmaceutically acceptable carriers, including sealed containers, or ingredients such as excipients. Advantageously the preparation may be presented in a unit dosage form, or as a sterile, sealed formulation. Preparations comprising a compound of formula (I) may be presented with a suitable carrier in formulations for parenteral (subcutaneous or preferably intramuscular), intravenous or oral administration. A sterile injectable formulation is advantageously formed in an organic carrier, which may also contain bacteriostatic agents, antioxidants, buffer solutes to render the preparation isotonic with the blood, thickening agents, suspending agents or other pharmaceutically acceptable additives.

The injectable formulations may be presented in unit dose containers, such as ampoules, or disposable injection devices, or in multi-dose forms such as bottles from which an appropriate dose may be withdrawn.

The formulations for oral administration may include as carriers solids to form tablets, pastes, granules or powder, or may include liquids for suspensions or solutions, which may contain diluents, binding agents, dispersing agents, surface active agents, lubricating agents, coating materials, colouring agents, solvents, thickening agents, suspending agents or other pharmaceutically acceptable additives, and these preparations may be present in unit dose form or multi-dose form, or as additives to foodstuffs. The compounds of formula (I) may also be formulated into a salt-lick so that the animals can obtain prophylactic treatment when in the field. Compounds of formula (I) can also be formulated into a pour-on preparation containing for example up to 10% by weight active compound in a suitable carrier such as dimethylsulphoxide.

According to a further aspect the present invention also provides a package composition for the protection and treatment of appropriate mammals against theileriosis, which comprises a preparation as hereinbefore defined together with instructions as to the usage of the same to achieve protection against or cure from the disease.

For therapeutic treatment the compound of formula (I), or a salt thereof may be administered as one relatively large dose on the day the temperature of the animal rises and schizonts appear or later in the disease syndrome that this, folllowed by similar daily doses for the next few days, for example 5 days. The total dosage over the treatment period is preferably from 0.5 to 50 mg/kg active ingredient, more preferably 0.5 to 10 mg/kg active ingredient, most preferably 1 to 5 mg/kg. The treatment may alternatively comprise a single dose or 2 doses administered on consecutive days, or could comprise up to a total of 10 doses.

In prophylactic treatment, for example when an animal is suspected of having been exposed to infection, the compound of formula (I) may be administered for instance as a dose of 1 to 5 mg/kg on the first day, followed by similar weekly doses up to a maximum of 5 doses. Depending on the severity of the risk of exposure, weekly doses of 0.2 to 5 mg/kg may be administered. The duration of such preventive measure may last from 4 to 20 or even 120 days. Alternatively, the compound can be incorporated into a slow release chronic implant, which is formulated into a pellet with a relatively insoluble carrier, so that it can be injected under the skin by means of a gun. As the pellet dissolves the active ingredient is released slowly over a period of for example 4 months, so that a low level of protection is maintained, which is equivalent to the above regimen.

According to a yet further aspect there is provided a method for treating theileriosis in cattle or sheep, either prophylactically or therapeutically or both, comprising the administration of an effective amount of a compound of formula (I) or a pharmaceutically acceptable salt thereof, to an animal infected or potentially exposed to an infection, with a pathogenic Theileria species. In particular the method of treatment can be effected by the use of a preparation or composition of such compounds, as hereinbefore defined.

In a further particular aspect the treatment as hereinbefore defined includes the administration of a vaccine, containing living Theileria organisms of one or more species or strains acting as effective antigens. Such vaccines for the purpose may for instance be prepared from a suspension of ground ticks, which have been infected by Theileria species, e.g. T.parva(parva) and T.Parva(lawrencei)(c.f.Radley. D. E. et al (1975), Veterinary Parasitology, 51–60) or other infected material, e.g. cultured mammalian cells infected with Theileria or cultured tick cells or salivary tissue or their products or exudates infected with Theileria. Conveniently, a dosage of an active compound hereinbefore described, representing 0.5 to 5 mg/kg of the host animal, is administered on the day of vaccination or up to 7 or even 14 days after vaccination. Thus the initial treatment can consist of the administration of a combination product which provides for an immediate release of the antigen, and a later release of the active compound delayed for seven or more days. The initial dosage may be followed by weekly dosages of 0.5 to 5 mg/kg. for up to 10 weeks.

EXAMPLE 1

Preparation of 2-/trans-(4-t-butylcyclohexyl)methyl/-3-hydroxy-1,4-naphthoquinone A. Preparation of 1-trans-(4-t-butylcyclohexyl)-acetic acid 4-t-Butylcyclohexane-1-carboxylic acid (50 g, mixture of cis and trans isomers), potassium hydroxide (150 g), and ethylene glycol (500 ml) were heated under reflux overnight. The reaction mixture was then poured onto crushed ice (2000 g), acidified with conc. hydrochloric acid, and the resultant white precipitate filtered off. The wet solid was dissolved in ethyl acetate, the water layer removed, and the organic layer dried over magnesium sulphate. Removal of solvent under reduced pressure gave a white solid, which on recrystallisation from toluene afforded 1-trans-(4-t-butyl-cyclohexyl)-carboxylic acid (30.9 g, m.p. 172–174).

The 1-trans-(4-t-butyl-cyclohexyl)-carboxylic acid (35 g), was dissolved in anhydrous ether (250 ml), and slowly added to a solution of lithium aluminium hydride (7.3 g) in anhydrous ether (200 ml), at such a rate as to maintain a gentle reflux. After addition was complete, the mixture was stirred and heated under reflux for a further 1½ hours. The reaction mixture was then cooled in an ice-bath and ice-cold hydrochloric acid (200 ml, 2N) added. The aqueous layer separated, washed with ether (100 ml), the combined organic extracts washed with dilute sodium hydroxide, then water, dried (magnesium sulphate), and solvent removed in vacuo to give a colourless oil, 28 g. The 1-trans-(4-t-butyl-cyclohexyl)-methanol from above, (28 g) was dissolved in dry acetonitrile (330 ml), anhydrous lithium bromide 28.7 g) and chlorotrimethylsilane (44.5 g) added and the mixture heated under reflux for 60 hr. The reaction mixture was then allowed to cool, and the solvent removed in vacuo. The residue was dissolved in ether, washed with water (100 ml), 10% sodium bicarbonate (100 ml), water (100 ml), dried (MgSO4), and the solvent removed under reduced pressure. Column chromatography of the crude product afforded 1-trans-(4-t-butylcyclohexyl)-methane bromide as an oil (15.5 g).

The above bromide (15 g) was added to sodium cyanide (4.83 g) in hexamethyl phosphorictriamide and stirred at ambient temperature overnight. The crude reaction mixture was diluted with water (250 ml), and extracted with ether (2×200 ml). The combined organic layers were washed with water (3×100 ml), dried (MgSO4) and the solvent removed in vacuo to give 1-trans-(4-t-butylcyclohexyl)methane nitrile as a colourless liquid (10.5 g).

1-Trans-(4-t-butylcyclohexyl)-methane nitrile (10 g), potassium hydroxide (20 g), ethanol (200 ml) and water (50 ml) were heated under reflux for 65 hours. Most of the solvent was removed in vacuo and the residue dissolved in water (300 ml), and extracted with ethyl acetate (100 ml). The aqueous layer was acidified with hydrochloric acid and extracted with ethyl acetate (2×100 ml). The combined organic layers were washed with water (200 ml), dried (MgSO4), and the excess solvent removed in vacuo, and the solid residue triturated with cold water, to yield 1-trans-(4-t-butylcyclohexyl)-acetic acid (9.5 g, m.p. 93°–95°).

B. Preparation of 2-/trans-(4-t-butylcyclohexyl)methyl/-3-hydroxy-1,4-naphthoquinone A mixture of 2-chloro-1,4-naphthoquinone (960 mg), 1-trans-(4-t-butylcyclohexyl)acetic acid (990 mg prepared by the method described in J. Amer. Chem. Soc. 1970,92,2800 or as described above) and silver nitrate (250 mg) in acetonitrile (9 ml) was heated to reflux with vigorous stirring whilst a solution of ammonium persulphate (3.0 g) in water (12 ml) was added dropwise over 1 hour. The mixture was refluxed for a further hour, cooled in ice and the yellow solid so obtained collected and washed with water. The solid was extracted with hot ethyl acetate which on cooling yielded 2-/(trans-(4-t-butylcyclohexyl)-methyl)/-3-chloro-1,4-naphthoquinone m.p. 154°–156° C. NMR spectroscopy confirmed that the 2-/trans-(4-t-butylcyclohexyl)methyl/-3-chloro-1,4-naphthoquinone, m.p. 154°–156° NMR spectroscopy confirmed that the material was 100% trans isomer.

Chloroquinone (6 g) obtained as described above, in dimethoxyethane (60 ml) and water (60 ml) was heated under reflux whilst potassium hydroxide (6.0 g) in water (60 ml) was added dropwise over 10 minutes. Reflux was continued for a further 15 minutes, the mixture cooled rapidly to ambient temperature and acidified with concentrated hydrochloric acid. The bright yellow solid so obtained was collected, washed with water and dried to yield 2-/trans-(4-t-butylcyclohexyl)methyl/-3-hydroxy-1,4-naphthoquinone m.p. 180°–182° C.

EXAMPLE 2

Preparation of 2-/cis-(4-t-butylcyclohexyl)methyl/-3-hydroxy-1,4-naphthoquinone By a method analogous to that of example 1, 2-chloro-1,4-naphthoquinone was treated with 1-cis-(4-t-butylcyclohexyl)-acetic acid, and the resultant chloroquinone hydrolysed to yield 2-/cis-(4-t-butylcyclohexyl)methyl/-3-hydroxy-1,4-naphthoquinone mp, 124°–125°.

EXAMPLE 3

Preparation of 2-/trans-(4'-t-pentylcyclohexyl)methyl/-3-hydroxy-1,4-naphthoquinone A: Preparation of 1-trans(4-t-pentylcyclohexyl)acetic acid Trans-t-pentylcyclohexane-1-carboxylic acid (8.0 g), dichloromethane (34.7 mls), and thionyl chloride (17.77 g) was stirred at ambient temperature for 22 hours. The reaction mixture was evaporated in vacuo to give a black residue which was distilled under reduced pressure to give trans-t-pentylcyclohexane-1-carboxylic acid chloride, 7.05 g, b.p. 107°–110°/0.5 mm Hg.

The above acid chloride, was then added, dropwise over 30 minutes to a solution of diazomethane in ether at 0°, and the solution left to stand in the refrigerator overnight. Evaporation of the excess solvent under reduced pressure gave the corresponding diazo-ketone as a yellow oil, 6.8 g.

The diazo-ketone (6.8 g) was dissolved in anhydrous methanol (60 ml), and a solution of silver benzoate (0.45 g), in triethylamine (7 ml) added, dropwise, with stirring. The solution was heated under reflux for 1 hour, allowed to cool, filtered through charcoal, and the filtrate evaporated to dryness under reduced pressure. Distillation of the resulting residue, afforded trans-t-pentylcyclohexylmethyl acetate, b.p. 94°–100°/0.2 mm Hg. The trans-t-pentylcyclohexylmethyl acetate (3.6 g) was dissolved in methanol (11 ml), a solution of sodium hydroxide (1.08 g) in water (5 ml) added, and the reaction mixture stirred at ambient temperature overnight. The reaction mixture was diluted with water (50 ml) and extracted with ether. The aqueous phase was acidified with concentrated hydrochloric acid and extracted with ether. The ether extracts were dried (magnesium sulphate) and evaporated in vacuo to give 1-trans-(4-t-pentylcyclohexyl)acetic acid as an oil (2.0 g).

B. Preparation of 2-/trans(4'-t-pentylcyclohexyl)methyl/-3-hydroxy-1,4-naphthoquinone A mixture of 2-chloro-1,4-naphthoquinone (0.95 g), 1-trans-(4-t-pentylcyclohexyl)-acetic acid (1.0 g), and silver nitrate (0.17 g) in acetonitrile (1.5 ml) was heated to reflux with vigorous stirring whilst a soltion of ammonium persulphate (1.7 g) in water (3 ml) was added dropwise over 1 hour. The mixture was heated under reflux for a further hour, cooled in ice, and then extracted into ether. The ether extract was washed with water, dried (magnesium sulphate) and evaporated to yield 2-/trans-(4'-t-pentylcyclohexyl)methyl/-3-chloro-1,4-naphthoquinone, 700. mg.

The chloroquinone (700 mg) obtained as described above in methanol (21 ml) was heated under reflux whilst potassium hydroxide (700 mg) in water (7 ml) was added dropwise over 10 minutes. Reflux was continued for a further 15 minutes, the mixture cooled rapidly in ambient temperature and acidified with concentrated hydrochloric acid. The mixture was extracted with chloroform, and washed throughly with water. The organic extracts were dried (magnesium sulphate) and evaporated in vacuo to yield an oil. Column chromatography on silica gel, eluting with toluene, followed by recrystallisation from acetonitrile, afforded 2-/trans(4'-t-pentylcyclohexyl)methyl/-3-hydroxy-1,4-naphthoquinone, 150 mg, m.p.132°–135°.

EXAMPLE 4

A "pour-on" formulation for cattle may be prepared as follows:

| | |
|---|---|
| 2-/trans-(4-t-butylcyclohexyl)methyl/3-hydroxy-1,4-naphthoquinone | 4 parts by weight |
| Dimethyl sulphoxide | 10 parts by weight |
| Castor oil | to 100 parts by weight |

EXAMPLE 5

An aqueous suspension may be prepared as follows:

| | |
|---|---|
| 2-/trans-(4-t-butylcyclohexyl)methyl/3-hydroxy-1,4-naphthoquinone | 1.00 parts by weight |
| Neosyl | 16.00 parts by weight |
| Bentonite | 3.20 parts by weight |
| Glycerin | 15.00 parts by weight |
| Sodium benzoate | 1.00 parts by weight |
| Bevaloid 35/2 | 1.00 parts by weight |
| Thymol | 0.04 parts by weight |
| Water | 62.76 parts by weight |
| | 100.00 |

EXAMPLE 6

A salt block may be prepared by mixing the finely divided 2-/trans-(4-t-butylcyclohexyl)methyl/-3-hydroxy-1,4-naphthoquinone (0.5 parts by weight) with sodium chloride (99.5 parts by weight) and the mixture pressed into blocks.

EXAMPLE 7

The following paste may be prepared:

| | |
|---|---|
| 2-/trans-(4-t-butylcyclohexyl)methyl/3-hydroxy-1,4-naphthoquinone | 3.0 parts by weight |
| Gum tragacanth | 4.0 parts by weight |
| Bevaloid 35/3 | 1.0 parts by weight |
| Nipagin "M" | 0.1 parts by weight |
| Glycerin | 19.0 parts by weight |
| Water | 72.9 parts by weight |
| | 100.0 |

EXAMPLE 8

A solution for subcutaneous injection may be prepared by mixing:

| | |
|---|---|
| 2-/trans-(4-t-butylcyclohexyl)methyl/3-hydroxy-1,4-naphthoquinone | 4.5 parts by weight |
| Methocel | 2.0 parts by weight |
| Nipagin "M" | 0.1 parts by weight |
| Water | 93.4 parts by weight |
| | 100.0 |

EXAMPLE 9

A solution for intramuscular injection may be prepared by mixing:

| | |
|---|---|
| 2-/trans-4-t-butylcyclohexyl)methyl/ 3-hydroxy-1,4-naphthoquinone | 9.5 parts by weight |
| Dimethyl sulphoxide | 19.0 parts by weight |
| Sorbitan monooleate | 4.5 parts by weight |
| Corn oil | 67.0 parts by weight |
| | 100.0 |

EXAMPLE 10

The following injectable formulation was prepared:

| | |
|---|---|
| 2-/trans-(4-t-butylcyclohexyl)methyl/ 3-hydroxy-1,4-naphthoquinone | 5 parts by weight |
| N—methyl-pyrollidone | 48.3 parts by weight |
| Tween 80 | 2 parts by weight |
| Span 80 | 4.7 parts by weight |
| Miglyol 812 | 40 parts by weight |
| | 100 |

EXAMPLE 11

In vitro activity against *T.parva* and *T.annulata*

In vitro results demonstrating the effectiveness of the compound of formula (I) wherein R=CH$_3$ against *T.parva* and *T.annulata* are shown in comparison with the known antithielerial 2-hydroxy-3-cyclohexyl-1,4-naphthoquinone. Cultures of bovine lymphoblastoid cells infected with the macroschizont stage of *T.parva* were incubated for 48 hours in the present of various concentrations of 2-/trans-(4-t-butylcyclohexyl)methyl/-3-hydroxy-1,4-naphthoquinone and 2-hydroxy-3-cyclohexyl-1,4-naphthoquinone. Other cultures were incubated without the drug to act as controls. Fourfold dilutions of compounds were assayed to determine ED50 values, at least two tests being conducted on each compound. The ED50 is the concentration of drug required (mg/L) to reduce the proportion of schizont-infected cells of the culture to 50% of that of untreated controls in the 48hr incubation period.

The results are given in Table 1.

TABLE 1

| Compound | ED50 (mg/L) | |
|---|---|---|
| | vs. T. parva | vs. T. annulta |
| Compound (I) R=CH$_3$ | 0.0002 | 0.005 |
| 2-hydroxy-3-cyclohexyl 1,4-naphthoquinone | 0.006 | 0.100 |

EXAMPLE 12

In vivo activity against *T.parva*

The effectiveness of 2-/trans-(4-t-butylcyclohexyl)-methyl/-3-hydroxy-1,4-naphthoquinone was demonstrated against *T.parva* in vivo and compared with the known anti-theilerial, 2-hydroxy-3-cyclohexyl-1,4-naphthoquinone.

Pure friesian steers weighing 180–250 kg and serologically negative for antibodies to *T.parva* were infected by the subcutaneous injection of 1.0 ml of stabilate 147 of *T.parva*. On the third day of significant pyrexia, 2-/trans-(4-t-butyl-cyclohexyl)-methyl/-3-hydroxy-1,4-naphthoquinone (as a formulation according to example 9), and 2-hydroxy-3-cyclohexyl-1,4-naphthoquinone (in a similar formulation), were injected intra-muscularly into 2 groups of friesian steers. The recovery of the different groups as compared to the control animals is shown in Table 2.

TABLE 2

| Treatment Group Parameter Dose: | Controls | 2-hydroxy cpd. (I) 3-cyclohexyl 1,4-naphthquinone 20 mg/kg | R=Me 5 mg/kg |
|---|---|---|---|
| No. in group | 5 | 5 | 5 |
| No. alive at day 28 | 0 | 5 | 5 |
| Days from CURE treatment to DEATH | 9.2 ± 1.46 | 7.4 ± 1.47 | 3.0 ± 0.45 |
| Severity of Theileriosis | 5 SF | 4 MR 1 IR | 5 MR |

M-mild, I-intermediate, S-severe, R-recovery F-fatal.

EXAMPLE 13

In vivo activity against *T. annulata*

Female Jersey calves, 115–140 kg body weight were infected by the injection of 0.8 ml of a stabilate prepared from homogenised ticks (*Hyalomma anatolicum anatolicum*) infected with the Hissar strain of *T. annulata* 2-/trans-(4-t-Butylcyclohexyl)methyl/-3-hydroxy-1,4-naphthoquine (as a formulation according to example 9), was administered into the neck muscles 12 days after infection. The recovery of the different groups and the control is shown in Table 3.

TABLE 3

| Parameter | 2-/trans-(4-t-butylcyclohexyl)methyl/ 3-hydroxy-1,4-naphthoquinone | | | Untreated Control |
|---|---|---|---|---|
| | 5 mg/kg | 2.5 mg/kg | 1.25 mg/kg | |
| Days to pyrexia | 10 | 11 | 12 | 11 |
| Duration of pyrexia in days post treatment (day 12) | 0 | 0 | 0 | 4 |

EXAMPLE A

Preparation of 4-t-alkyl-cyclohexane carboxylic acids

The carboxylic acids used in the following examples were prepared as follows:

(i) 4-t-Butylcyclohexane-1-carboxylic acid, 4-t-butylcyclohexylacetic acid, and the pure cis and trans isomers thereof were either obtained commercially or as described in the literature (J.Amer.Chem.Soc. 1970, 92, 2800 and references therein).

(ii) 4-t-Pentylcyclohexyl-1-carboxylic acid (cis/trans mixture) and pure trans 4-t-pentylcyclohexyl-1-carboxylic acids were obtained as follows:

(a) Preparation of cis/trans-4-t-pentylcyclohexyl-1-carboxylic acid 4-t-pentylcyclohexane (49.2 g) was dissolved in ether (200 ml), and sodium cyanide (24.46 g) and water (30 ml) added. The mixture was cooled to 0° and stirred vigorously while concentrated hydrochloric acid was added dropwise over 1 hour. Stirring was continued for a further 3 hours and the mixture was then allowed to stand overnight. The reaction mixture was washed with saturated sodium metabisulphite (2×200 ml) and the ether layer dried over sodium sulphate. Removal of solvent in vacuo afforded the cyanohydrin as a pale yellow oil, 54.0 g.

The cyanohydrin (54.0 g) was dissolved in anhydrous pyridine (70 ml) and anhydrous benzene (70 ml), stirred and cooled to 0°. Phosphoryl chloride (90 ml) in pyridine (83 ml) was added, dropwise over 45 mins., whilst the temperature was kept at 0°. The reaction mixture was allowed to warm to reflux for a further 30 mins. The mixture was allowed to cool, poured onto ice, stirred for 30 mins., and then extracted with ether, washed with water, dried (sodium sulphate) and evaporated to dryness in vacuo to yield 4-t-pentylcyclohex-1-ene-1-nitrile, 48.4 g, as an oil. 1-4-t-Pentylcyclohex-1-ene-1-nitrile (48.0 g) was added to a mixture of potassium hydroxide (23.3 g) in water (34 ml) and ethanol (150 ml). The mixture was heated under reflux for 72 hours, cooled in ice, diluted with water (175 ml) and then acidified with concentrated hydrochloric acid. A colourless solid was precipitated filtered, washed with water, and dried (sodium sulphate). The solid was partitioned between ethyl acetate and sodium hydroxide solution (2N), the basic layer was separated and acidified with concentrated hydrochloric acid, and the resultant colourless solid collected by filtration, washed with water, and dried to give 4-t-pentylcyclohex-1-ene-1-carboxylic acid, 33.65 g, mp 123°–125°.

4-t-Pentylcyclohex-1-ene-1-carboxylic acid (33.5 g) was dissolved in ethanol (275 ml), and 10% palladium on charcoal (1.0 g), added. The mixture was hydrogenated at 10 atm until the theoretical value of hydrogen had been taken up. The catalyst was filtered off and the colourless filtrate evaporated to dryness in vacuo to give 4-t-pentylcyclohexyl-1-carboxylic acid, as an oil, 27.0 g (cis/trans mixture).

(b) Preparation of pure trans-4-t-pentylcyclohexyl-1-carboxylic acid

The cis/trans mixture of acids (12 g, prepared by method (a) above) was heated in a steam bath in the presence of concentrated sulphuric acid (60 ml) for 16 hours. The reaction mixture was cooled, poured onto ice and a black solid formed. The solid was filtered, and dried and then triturated with light petroleum (40°–60°) until most of the solid had dissolved. The petroleum extract was treated with charcoal and then evaporated to dryness in vacuo to yield trans-1-4-t-pentylcyclohexyl-1-carboxylic acid, 5.7 g, mp 92°–100°. NMR spectroscopy showed the product to be 95–97% pure trans isomer.

We claim:

1. A compound of the formula (I)

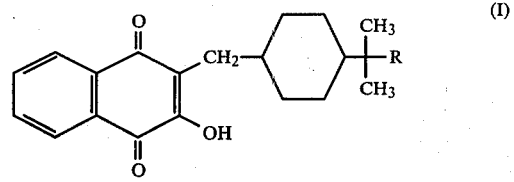

wherein R is a $C_1$ to $C_{10}$ alkyl group, and pharmaceutically acceptable salts thereof.

2. A compound according to claim 1 wherein R is a straight chain alkyl group.

3. A compound according to claim 1 wherein R is a straight chain $C_1$ to $C_4$ alkyl group.

4. A compound according to claim 1 wherein R is a methyl group.

5. A compound according to claim 1 wherein R is an ethyl group.

6. A compound according to claim 1 in the form of a mixture of cis and trans isomers.

7. A compound according to claim 6 wherein the ratio of isomers is about 1:1.

8. A compound according to claim 1, in the form of the pure trans isomer.

9. A compound according to claim 1 in the form of the pure cis isomer.

10. A therapeutic formulation comprising a non-toxic, effective anti-protozoal amount of a compound of formula (I) as defined in claim 1, together with a therapeutically acceptable carrier therefor.

11. A method for the treatment of a protozoal infection in an animal comprising administration of an effective anti-protozoal, non-toxic amount of a compound of formula (I) as defined in claim 1.

12. A method according to claim 11 where the protozoal infection is a *Theilerial* infection.

13. A method according to claim 12 where the protozoal infection is a *Theileria annulata* or a *Theileria parva(parra)* infection.

14. A method according to claim 11 wherein the amount of the compound of formula (I) is from 0.5 to 50 mg/kg bodyweight of the animal.

15. A method according to claim 12 wherein the amount of the compound of formula (I) is from 0.5 to 50 mg/kg bodyweight of the animal.

16. A method according to claim 13 wherein the amount of the compound of formula (I) is from 0.5 to 50 mg/kg bodyweight of the animal.

* * * * *